United States Patent [19]

Valentine

[11] Patent Number: 5,593,889

[45] Date of Patent: Jan. 14, 1997

[54] BIODESULFURIZATION OF BITUMEN FUELS

[76] Inventor: James M. Valentine, 480 Hemlock Rd., Fairfield, Conn. 06430

[21] Appl. No.: 538,254

[22] Filed: Oct. 3, 1995

Related U.S. Application Data

[63] Continuation of Ser. No. 308,191, Sep. 19, 1994, abandoned, which is a continuation of Ser. No. 78,989, Jun. 16, 1993, abandoned, which is a continuation-in-part of Ser. No. 616,610, Nov. 21, 1990, abandoned.

[51] Int. Cl.$^6$ ........................................ C10C 3/00
[52] U.S. Cl. ........................................ 435/282; 435/262
[58] Field of Search ........................ 435/262, 281, 435/282; 44/622, 624, 623; 252/312, 311.5

[56] References Cited

U.S. PATENT DOCUMENTS

| | | | |
|---|---|---|---|
| 2,521,761 | 9/1950 | Strawinski | 195/3 |
| 2,574,070 | 11/1951 | Strawinski | 195/3 |
| 2,641,564 | 6/1953 | Zobell | 195/3 |
| 2,975,103 | 3/1961 | Kirschenbaum | 195/3 |
| 4,562,156 | 12/1985 | Isbister et al. | 435/253 |
| 4,618,348 | 10/1986 | Hayes et al. | 44/51 |
| 4,632,906 | 12/1986 | Kopacz | 435/282 |
| 4,659,670 | 4/1987 | Stevens et al. | 435/262 |
| 4,795,478 | 1/1989 | Layrisse et al. | 44/51 |
| 4,808,535 | 2/1989 | Isbister | 435/282 |
| 4,824,439 | 4/1989 | Polanco et al. | 44/51 |
| 4,851,350 | 7/1989 | Stevens, Jr. et al. | 435/262 |
| 4,861,723 | 8/1989 | Madgavkar | 435/262 |
| 5,002,888 | 3/1991 | Kilbane | 435/252.31 |
| 5,104,801 | 4/1992 | Kilbane | 435/282 |
| 5,122,353 | 6/1992 | Valentine | 423/244 |
| 5,132,219 | 7/1992 | Kilbane | 435/195 |
| 5,232,854 | 8/1993 | Monticello | 435/282 |
| 5,344,778 | 9/1994 | Kilbane | 435/262 |
| 5,356,813 | 10/1994 | Monticello | 435/282 |
| 5,358,869 | 10/1994 | Kilbane | 435/282 |
| 5,387,523 | 2/1995 | Monticello | 435/282 |
| 5,468,626 | 11/1995 | Johnson et al. | 435/130 |
| 5,472,875 | 12/1995 | Monticello | 435/282 |

OTHER PUBLICATIONS

Andrews and Maczuga, Biotechnol. Bioeng. Sym. 12, 337–348 (1982).

Bhattacharyya, Khalid, Hsieh, Kermode, and Aleem; Bioprocessing of Coal and Model Compounds; U.S. Department of Energy Contract No. DE–FC2289PC89851; Contractors Meeting, Oct. 3–4, 1989.

Kargi and Robinson, Biological Removal of Pyritic Sulfur from Coal by the Thermophermophilic Organism *Sulfolobus Acidocaldarius*, Biotech. and Bioeng., vol. 27, Jan. 1985, pp. 41–49.

Kilbane, J. Biodesulfurization: Future Prospects in Coal Cleaning, 7th Annual International Pittsburgh Coal Conference Proceedings, Sep. 1–14, 1990, pp. 373–382.

Kilbane, J. Desulfurization of Coal: The microbial Solution, Trends in Biotechnology, Apr. 1989, vol. 7, No. 4, pp. 97–101.

Lee and Yen, Sulfur Removal from Coal Through Multiphase Media Containing Biocatalysts, J. Chem. Tech. Biotechnol., 1990, vol. 48, pp. 71–79.

Monticello and Finnerty, Microbial Desulfurization of Fossil Fuels, Ann. Rev. Microbiol. 1985, 39:371–89.

*Primary Examiner*—Carolyn Paden
*Attorney, Agent, or Firm*—St. Onge Steward Johnston & Reens LLC

[57] ABSTRACT

A simple and effective biochemical process solves the problems associated with sulfur in bitumen by removing sulfur from active participation in $SO_x$-producing combustion reactions. In one aspect, an emulsion of bitumen and water is contacted with a microbiological desulfurization agent for a time and under conditions effective to reduce the oxidizable sulfur content of the bitumen. The preferred agents do not affect the heating value of the fuel, but selectively oxidize organic sulfur to water-soluble sulfates which can either be physically removed or chemically bound so that they do not cause $SO_x$ production. Multistage reaction is employed to enhance sulfur removal.

20 Claims, 1 Drawing Sheet

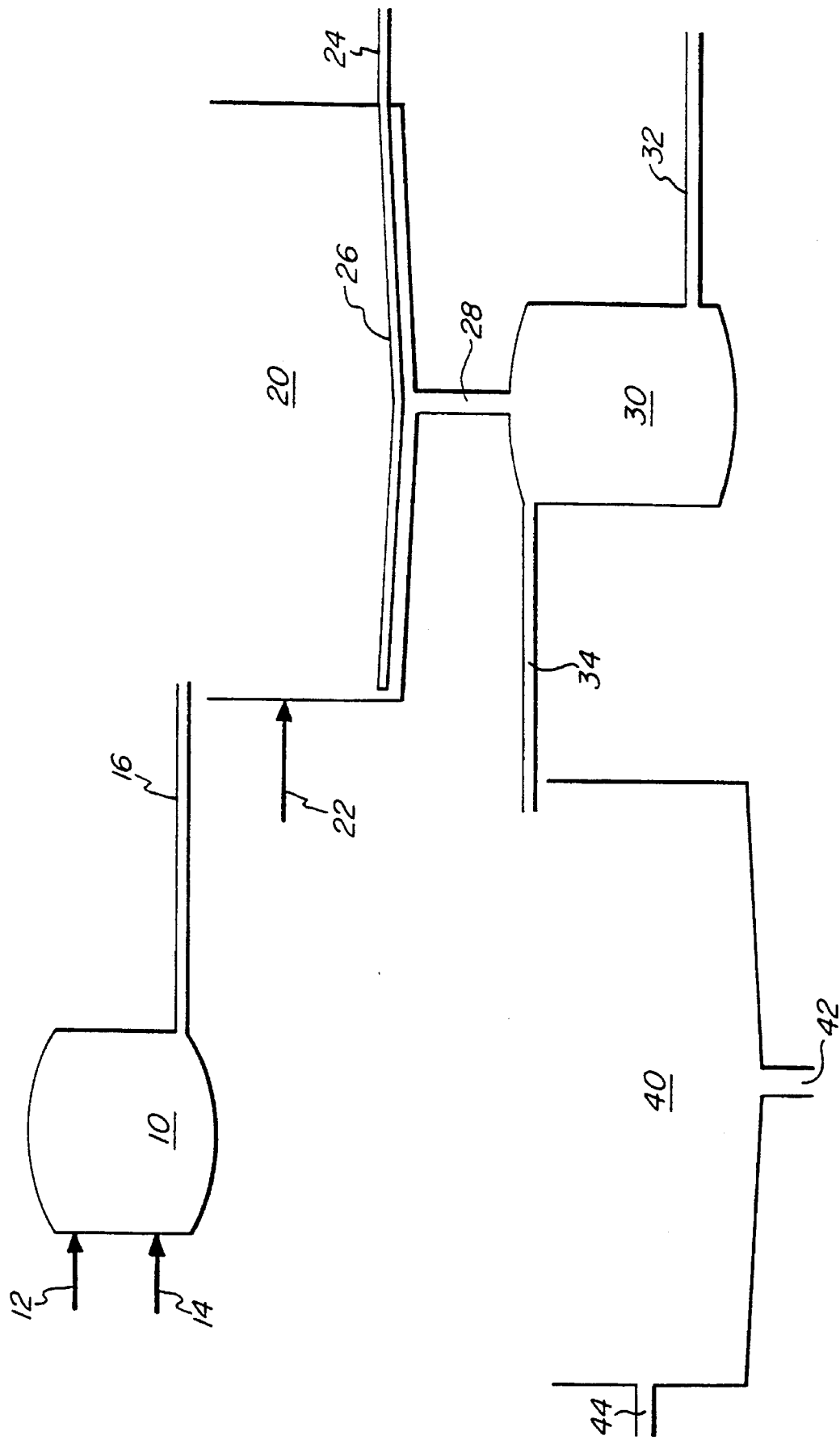

BIODESULFURIZATION OF BITUMEN FUELS

RELATED APPLICATION

This application is a continuation of U.S. patent application Ser. No. 08/308,191, filed Sep. 19, 1994, now abandoned, which was a continuation of application Ser. No. 08/078,989 filed Jun. 16, 1993, now abandoned, which was a continuation-in-part of patent application U.S. Ser. No. 07/616,610, filed Nov. 21, 1990, now abandoned, by James M. Valentine.

TECHNICAL FIELD

The invention relates to the desulfurization of carbonaceous fuels by microorganisms. More particularly, the invention enables the removal of sulfur by biotechnical means from emulsified fuels containing bitumen and water.

The removal of sulfur from various carbonaceous fuels including petroleum oils, coal and coal/petroleum mixtures is known, but the implementing technology for these fuels has not been adaptable to bitumen. These bitumens are of tar-like consistency and are not crude oils when viewed by either legal or practical engineering considerations. These materials are not solid like coal at ambient temperatures, in that they generally have pour points in the range of 5° to 50° C.; however, unless emulsified, they are not liquid at 15° C., typically requiring heating to 70° to 90° C. to be treated as a liquid. These bitumens are finding application in the form of emulsions where water is employed as a minor component but forms the continuous phase.

Unfortunately, despite their relative economy, abundance and desirable properties, these fuels often have sulfur contents which make them too environmentally expensive to use. Moreover, this is, in some fuels, coupled with high vanadium contents which can cause slagging and corrosion problems when burned.

It would be desirable to have a process which permitted efficiently treating bitumens to reduce these problems on a large scale and at reasonable cost.

BACKGROUND ART

The development of bitumen-in-water emulsions has provided renewed interest in burning vast stores of viscous hydrocarbons, variously called bitumen, native bitumen, tar, natural asphalt, viscous crude oil and heavy crude. See in this regard the paper *Evaluation of Handling & Combustion Characteristics of A Bitumen-in-Water Emulsified Fuel in a Commercial Utility Boiler* presented in December 1989 by Blair A. Kennedy at the Power-Gen '89 Conference. See also, U.S. Pat. No. 4,618,348 to M. E. Hayes et al. One commercially available bitumen-in-water emulsion product, known as Orimulsion, is made with about 70% Venezuelan Orinoco crude and about 30% water. Reserves of Orinoco crude are estimated at 1.2 trillion barrels, but it typically has high sulfur and vanadium contents which deter widespread commercialization.

The removal of sulfur, though desirable to limit the emissions of $SO_x$ compounds to the atmosphere during combustion, has to date been so impractical in terms of complexity of proposed reactors and reagents that none have been applied to bitumen. The oxides of sulfur are, however, known to contribute to the formation of acid rain and their removal must be taken into account in any economic study. Removal of contaminants prior to combustion would be particularly advantageous because these contaminants are more concentrated prior to their reaction with oxygen to form $SO_x$ compounds during combustion. The removal of $SO_x$ compounds by post-combustion methods involves the treatment of higher molecular weight compounds entrained in high-temperature, high-volume flue gases and requires that substantial capital and operating costs be applied to each major source of combustion. Yet, no practical method is available for precombustion removal of organosulfur compounds from bitumens, and the art has focused on post-combustion techniques which themselves cause difficulties in terms of solid disposal.

Pre-combustion removal of contaminants would have the advantage of being conducted on the preoxidized state of the contaminant. Pre-combustion techniques could be conducted at any point in the fuel handling and distribution stream prior to combustion. Pre-combustion treatment methods proposed for coal and light petroleum fractions have involved physical, chemical and biological treatments. Unfortunately, much of the offending sulfur compounds cannot be removed physically, and chemical treatment requires large investments in capital and high operating costs due to the use of hydrogen, solvents or the like.

For petroleum oils and coals, prior workers have attempted to remove both pyritic and organic sulfur through the use of microbial techniques. For a recent review of this, see Monticello and Finnerty, "Microbial Desulfurization of Fossil Fuels", *Ann. Rev. Microbiol.* 1985 (39:371–89). The discussion is primarily directed to the underlying biochemistry, not to the practical implementation of it, especially for bitumens which pose unique handling and processing problems. See also, Lee and Yen, "Sulfur Removal from Coal Through Multiphase Media Containing Biocatalysts", *J. Chem. Tech. Biotechnol.*, 1990, vol. 48, pp.71–79.

Several early patents have described large-scale processes for removing sulfur from low-viscosity oils. For example, in U.S. Pat. No. 2,521,761, Strawinski discloses using any of a variety of known microorganisms, but employs a "diverter" as carbon source as an alternative to the petroleum. Unfortunately, the diverter such as sugar or starch is costly. Later, in U.S. Pat. No. 2,574,070, Strawinski disclosed first converting sulfur to sulfates and then removing the sulfates in a second stage microbiological reaction by converting them to hydrogen sulfide. In U.S. Pat. No. 2,641,564, Zobell also teaches using a microbiological catalyst to remove sulfur from petroleum by reaction with hydrogen to produce hydrogen sulfide. These reactions are necessarily conducted on liquid petroleum and require the use of complex gas-liquid contact devices and produce large quantities of foul-smelling and dangerous by-products.

Other processes have also failed to be implemented because they did not offer the promise of economical operation. In U.S. Pat. No. 2,975,103 Kirshenbaum teaches contacting liquid petroleum with aerobic bacteria in a liquid-liquid contact column to oxidize the sulfur to sulfates and then removing the sulfates by precipitation with CaO, BaO or the hydroxides. This process, while requiring sophisticated equipment for operating on liquid oils could not be expected to operate on bitumen which is not liquid at temperatures effective for most biochemical reactions.

Similarly, in U.S. Pat. No. 4,861,723, Madgavkar treats coal with microorganisms and follows the reaction with a required step of removing the aqueous phase prior to combustion.

It would be desirable to provide a process capable of removing sulfur from bitumen which could be implemented without complex and costly equipment or the use of expensive or hazardous chemicals. It would be especially desirable if these criteria could be met to produce a fuel which could be burned without any requirement that the aqueous phase be removed prior to combustion.

DISCLOSURE OF INVENTION

The invention provides a simple and effective solution to the problems associated with sulfur in bitumen, thereby making large quantities of fuel available for use in the production of power and for other purposes, including refining, without sacrificing environmental or economic objectives. In one broad aspect, the invention provides a process for desulfurizing bitumen having a kinematic viscosity of at least about 10,000 centistokes at 50° C., comprising: contacting a bitumen-in-water emulsion with a microbiological desulfurization agent selected from the group consisting of cell cultures, immobilized cell masses, fragmented cells, cell extracts, enzyme mixtures, synthetically prepared copies of active enzyme sequences or components, and mixtures of these; and, maintaining contact at a temperature of less than about 50° C. for a time and under conditions effective to reduce the oxidizable sulfur content of the bitumen.

The emulsions are preferably of the bitumen-in-water type. Following reaction, at least a portion of the original sulfur content of the bitumen has been converted to sulfates which concentrate in the aqueous phase of the emulsion, in the water and/or the cells. The treated fuel can be treated to remove these sulfates from $SO_x$-creating combustion reactions by either physically separating these materials or rendering them chemically incapable of the offending reactions by the addition of a suitable chemical agent during or following the reaction.

BRIEF DESCRIPTION OF THE DRAWING

The invention will be better understood and its advantages will become more apparent when the following detailed description is read in connection with the attached drawing wherein:

The FIGURE is a schematic flow diagram showing a preferred process scheme according to the invention.

BEST MODE FOR CARRYING OUT THE INVENTION

This description details several of the more preferred aspects of the invention, but it is to be understood that the invention has wide applicability. For example, while small-scale reactions are described and exemplified, it is to be understood that the principal utility of the technology of this invention is its ready adaptability to large-scale processing as would be necessary to treat the large quantities of bitumen which may be held in ocean-going tankers, within pipelines during transport of the fuel, underground storage facilities such as are now employed by the United States government as a strategic petroleum reserve, aerated stirred reactors of the type typically employed to treat domestic sewage, and the tanks in tank farms.

The process of the invention provides a simple and effective solution to the problems associated with sulfur in bitumen. In one broad aspect, the process comprises contacting an emulsion of highly viscous bitumen in water with a microbiological desulfurization agent and maintaining contact at a temperature too low to achieve contact between bitumen and the desulfurization agent in a typical chemical reactor of the liquid—liquid contact type. Achieving contact in a liquid—liquid reactor would require heating the bitumen above the reaction temperature of the desulfurization agent. According to the invention, however, contact is enabled, as it has not been in the past, for a time and under conditions effective to reduce the oxidizable sulfur content of the bitumen. The mixtures of oil and water in conventional liquid—liquid contact apparatus are not stable emulsions and energy must be constantly expended, at high levels, to maintain dispersion. This is costly and can damage live cells. The invention provides stable emulsions (e.g. at least 1 day without significant separation) which are agitated only as desired to mix air, nutrients, substrates and desulfurization agent. The invention not only enables effective contact between the bitumen and the desulfurization agent, it provides a process adaptable to high-volume equipment for economical sulfur reduction.

Following reaction, at least a portion of the original sulfur content of the bitumen has been converted to sulfates which concentrate in the aqueous phase of the emulsion. The treated fuel can be treated to remove these sulfates from $SO_x$-creating combustion reactions by either physically separating these materials or rendering them chemically incapable of the offending reactions by the addition of a suitable chemical agent during or following the reaction.

Reference is now made to the FIGURE which shows a preferred process scheme according to this invention. The FIGURE shows schematically several alternatives which can be applied to bitumens derived from any source, including the fields known to produce such in North America, Mexico, Venezuela or the Middle East. These bitumens typically have high densities, with API gravities as low as 10 degrees and less, e.g. about 7 to about 9 degrees API. Sulfur contents of up to 5% are not uncommon, and of from 1 to 4% are typical. This can be present in the form of inorganic and/or organic sulfur, and the present invention can be employed to facilitate the treatment of bitumen such that the $SO_x$-potential of either or both is reduced.

The bitumen can be passed to an emulsifier 10 which can be any device effective for the purpose. The emulsions are preferably of the bitumen-in-water type. It is within the contemplation of the invention to employ complex emulsions with the attributes of both bitumen-in-water and water-in-bitumen emulsions. There are good reasons in some situations to employ one of these other emulsion forms.

Bituminous hydrocarbons, because of their highly viscous nature, typically require extraordinary means to remove them from wells. In the case of Orinoco crude from Venezuela, water and surfactants (sometimes with steam) is pumped into the wells to soften and emulsify the bitumen. The emulsions are pumped to the surface where the emulsions of bitumen in water are broken (typically by heating under pressure) separated into bitumen and water phases, and reemulsified such as in emulsifier 10. Emulsions of Orinoco crude are commercially available under the trademark Orimulsion. These are stable bitumen-in-water emulsions and do not normally require reemulsification prior to processing according to the invention. This is, however, not a rigid rule, and there may be reason, for example, for removing at least a portion of the water phase and replacing it with one more compatible with the objectives of this invention.

Representative of the technology which can be employed to prepare emulsions of bituminous hydrocarbons is that described in U.S. Pat. No. 4,618,348, to Hayes et al, the disclosure of which is incorporated herein by reference.

In preparing suitable emulsions of bitumen in a continuous aqueous phase, the bitumen can be emulsified through the addition of any amount of water effective to form the emulsion. Typically, from 30 to 70% water (by volume of the final emulsion) is added (as by line 12) and the bitumen (added by line 14) is thoroughly and finely dispersed therein. Where greater amounts of water are desired (up to about 10 times these amounts, e.g., 2 to 5 times), it may be more efficient to add only a portion prior to emulsification, and simply blend in the remainder later. Effective dispersion is achieved by suitable devices, such as rotary (e.g., centrifugal pumps), mechanical, or static, dynamic or other emulsifying devices. Desirably the bitumen is heated to a fluid state prior to emulsification. Any one of a number of known chemical or biological surfactants can be added to ensure the stability of the bitumen-in-water emulsion, with water being the continuous phase.

It is preferred to obtain droplet sizes effective to provide a high surface area of contact between the desulfurization agent and the bitumen during reaction. This is important to both the reaction rate and to the degree of reaction which can be achieved since reactions take place at the bitumen-water interface. Fine dispersion helps to maximize the chance that the sulfur content of the individual bitumen droplets will be contacted by the desulfurization agent during the entire reaction period. It is preferred to obtain mean droplet sizes below about 250 microns, and more preferably in the range of 10 to 100 microns. This size range allows effective surface area for reaction while also assuring stability of the emulsion at reasonable energy input and surfactant levels. Desirably, less than 5% of the droplets will be in excess of 100 microns, and preferably this will be kept to less than 2%.

While it is conceivable that desulfurization agents could be added to the aqueous phase during preparation of the oil-in-water emulsion, it is preferable that the emulsion be passed first to a separate desulfurization zone, shown as 20 in the FIGURE, such as by line 16. When additional water is desired it can be added to the desulfurization zone 20 with additional nontoxic surfacants and nutriments as necessary. The zone 20 can include any reactor capable of holding large volumes of emulsion while agitating and aerating.

The reaction is initiated by introducing into the water phase of the emulsion a microbiological desulfurization agent (such as via line 22) which can be any biological organism, living or dead, any biologically produced enzyme or sequence of enzymes, cellular matter of an organism, or chemically-synthesized equivalent that is capable of reacting with the sulfur in the bitumen, preferably by oxidizing it to sulfate. Among the various forms of microbiological desulfurization agents are those selected from the group consisting of cell cultures, immobilized cell masses, fragmented cells, cell extracts, enzyme mixtures, synthetically-prepared copies of active enzyme sequences or components, and mixtures of these.

Immobilized cell masses are prepared by aggregation, adsorption, or entrapment by means known in the art and have the advantage that they can be more easily separated from the water phase and can be more stable to osmotic shock or exposure to sunlight. Fragmented cells are prepared by maceration, sonification or osmotic shock to open at least a portion, e.g. above about 25%, of the cells to release the functional enzymes, emulsifiers and other active agents. Cell extracts are prepared from fragmented cells by a step of centrifugation or the like to achieve an extract fraction rich in active components.

The preferred agents are capable of cleaving carbon-sulfur bonds in bitumen, and particularly in emulsion form. The preferred desulfurization agents react with the bitumens such that the organic sulfur contained in them is released to the aqueous phase of the preferred bitumen-in-water emulsions. While a mixture of agents can be employed, to act on inorganic and organic sulfur with the modest utilization of carbon, the more preferred agents do not substantially affect the heating value of the fuel, but selectively oxidize organic sulfur to water-soluble sulfates which can either be physically removed or chemically bound so that they do not cause $SO_x$ production during combustion. It is, indeed, a major advantage of this invention that some fuels can be treated and directly burned with decreased $SO_x$ production, with no need to separately remove the metabolic residues of the sulfur when chemically bound.

Any of the organisms effective for reacting with the sulfur content of bitumen can be employed. Specifically identified as useful are the following:

| MICROORGANISM | REFERENCE |
| --- | --- |
| Pseudomonas sp. CB1 ATCC No. 39381 | U.S. Pat. No. 4,562,156 |
| Mixed culture ATCC No. 39327 | U.S. Pat. No. 4,659,670 |
| Acinetobacter sp. CB2 ATCC No. 53515 | U.S. Pat. No. 4,808,535 |
| Mixed culture | U.S. Pat. No. 4,851,350 |
| B. Sulfasportare ATCC No. 39909 | U.S. Pat. No. 4,632,906 |
| Mixed culture IGTS7 | Kilbane, Desulfurization of coal: the microbial solution, Trends in Biotechnology, April 1989, vol. 7, no. 4, pp. 97–101 |
| Rhodococcus rhodochrous IGTS8 ATCC No. 53968 | U.S. Pat. No. 5,104,801, and Kilbane, Biodesulfurization: Future Prospects in Coal Cleaning, Seventh Annual International Pittsburgh Coal Conference Proceedings, Sept. 10–14, 1990, pp. 373–382 |
| B. sphaericus IGTS9 ATCC No. 53969 | U.S. Pat. No. 5,002,888 and Kilbane, Biodesulfurization, supra. |
| Sulfolobus brierleyi | Bhattacharyya, Khalid, Hsieh, Kermode, and Aleem; Bioprocessing of Coal and Model Compounds; U.S. Department of Energy Contract No. DE-FC2289PC89851; Contractors Meeting, Oct. 3–4, 1989 |
| Pseudomonas putida | Bhattacharyya, Khalid, Hsieh, Kermode, and Aleem; Bioprocessing of Coal and Model Compounds; U.S. Department of Energy Contract No. DE-FC2289PC89851; Contractors Meeting, Oct. 3–4, 1989 |
| Mixed culture Oil-2 | Bhattacharyya, Khalid, Hsieh, Kermode, and Aleem; Bioprocessing of Coal and Model Compounds; U.S. Department of Energy Contract No. DE-FC2289PCB9851; Contractors Meeting, Oct. 3–4, 1989 |
| Sulfolobus acidocaldarius | Kargi and Robinson; Biological Removal of Pyritic Sulfur From Coal by The Thermophermophilic Organism Sulfolobus Acidocaldarius, Biotech. and Bioeng., vol. 27, Jan. 1985, pp. 31–49 |
| Thiobacillus ferrooxidans | Andrews and Maczuga, Biotechnol. Bioeng. Symp., 12, 337 (1982) |
| Mixed culture of T. ferrooxidans and T. thiooxidans | Andrews and Maczuga, Biotechnol. Bioeng. Symp., 12, 337 (1982) |

The above references are incorporated herein by reference in their entireties. In addition to this relatively short list are those agents cited or otherwise referred to in the references identified by this application, all of which are incorporated herein by reference. Additionally, other microbiological desulfurization agents which meet the objectives of the invention can be employed whether now known or which will be later developed.

The reaction is conducted in any suitable reaction vessel or containment device 20 by maintaining contact between the desulfurization agent and the bitumen for a time and under conditions effective to reduce the oxidizable sulfur content of the bitumen. As noted above, it is an advantage of the invention that bitumen which is not a flowable liquid until heated to well above 50° C can be reacted below this temperature in a range effective for the microorganisms.

The desulfurization zone can include storage, transport or intermediate processing vessels (including pipelines) as long as conditions are maintained to sustain microorganism or other agent activity. Nutrients are added as necessary to support the growth of microorganisms. Similarly, the pH is adjusted as necessary and aeration such as via line 24 and sparging apparatus 26 may be used to serve as a supply of oxygen and/or carbon dioxide for the microorganisms. In addition to mixing by gas sparging, it is also desired to provide additional mixing shear to better distribute the gas within the reaction vessel and to reduce any tendency for gas bubbles to inhibit the reaction. The reactor can be enclosed or covered for off-gas recovery, temperature control and the like. A preferred form of reactor 20 is an open reactor vessel of the type and size used to treat domestic sewage. Typical reactors of this type are at least partially supported by being below ground level and employ an agitation device in addition to a sparger which supplies air.

Contact of the bitumen with the desulfurization organism or other agent is made at conditions effective for the reaction and will, like the supply of nutrients, pH adjustment, temperature, aeration, and the like, depend on the particular desulfurization agent employed. For many of the useful agents, values for these parameters are known and for the others they can be readily determined by those skilled in the art. Temperatures of from about 15° C. to about 90° C. will generally be effective, and are most typically in the range of from about 20° C. to about 35° C.

While thermophilic organisms are known and have advantages in terms of high temperature operation, reaction at temperatures above about 80° C. requires special precautions to assure against excessive water loss, heating costs, and emulsion disruption. For most cases, practical temperatures are below 100° C. It is a particular advantage of the invention that bitumens that have such high viscosities (e.g. kinematic viscosities above about 10,000 centistokes at 50° C.) that they do not flow at reaction conditions most effective for the organisms, can be effectively processed at temperatures below 50° C. Indeed, it is an advantage of the invention that the economical treatment of low-grade bitumens is enabled by simple equipment such as large open stirred reactors and clarifiers of the type used for treatment of domestic sewage.

The reaction will be continued for a period of time sufficient to at least partially desulfurize the bitumen. Generally, time periods of under 120 days, e.g. less than 30 days will usually be adequate. There is typically no need to continue the reaction for this long. Conversely, there is usually no reason to stop the reaction at any particular time where the organisms do not degrade other aspects of the fuel. More typical reaction times will be encompassed in the range of from about 10 hours to about 300 hours of contact.

The contact of the bitumen with the organisms desirably results in a bitumen with a sulfur content of less than two percent and preferably one percent or less.

Following reaction, or one stage of reaction, the emulsion can be at least partially broken to produce a separable aqueous layer containing the majority of the desulfurization agent and sulfate oxidation products. The aqueous layer can then be separated from the bitumen, and the bitumen then reemulsified.

During biochemical desulfurization, sulfur is transferred from the bitumen to the aqueous phase of the emulsion. The emulsion can be passed via line 28 to a separation zone 30 wherein separation is accomplished using known emulsion breaking techniques including the use of pressure, temperature, settling, centrifugation, chemical deemulsifiers or any combination. This results in the separation of desulfurized bitumen from the water, sulfates and organisms. The bitumen can be withdrawn as via line 32 for storage, reemulsification, refining, or burning.

In one preferred form of the invention, the addition of water treatment agents (chemical sulfate binding agents) such as alkaline calcium, magnesium, aluminum, barium, and like metal compounds such as the oxides, hydroxides, and carbonates in effective amounts will eliminate the need to break the emulsion for the purpose of removing the sulfur metabolites, such as sulfates. These and other treatment agents are employed to chemically bind the sulfates thereby removing them from $SO_x$ formation. They can also be added in excess of sulfate such that $SO_x$ produced by unreacted sulfur is neutralized. These agents can be employed stagewise to most effectively react with the sulfates in solution. Magnesium-containing treatment agents, e.g. magnesium oxide and magnesium hydroxide, have the desirable added advantage of decreasing problems associated with vanadium. It is also possible to add these or other agents in the form of organic salts, such as the soluble salts of calcium, magnesium, or sodium with organic acids such as formic, acetic, propionic, butyric, and the like.

In another preferred form of the invention, the reaction is carried out in a plurality of stages, e.g. from 2 to 10, and typically less than 5. For each stage, the reaction is brought to partial completion, the emulsion is at partially broken, and the bitumen is worked effectively (separately or during reemulsification) to bring a fresh layer of sulfur compounds to the surfaces of the individual droplets. Reaction conditions, other than time, will closely follow those for single stage reactions.

In another preferred form of the invention, the cell culture is saved for reuse in a subsequent reaction or reaction stage, but is treated as by maceration or other known technique to obtain a cell extract which is then employed alone or in combination with another desulfurization agent for a subsequent reaction or reaction stage. This technique is especially advantageous when used to prepare a fuel emulsion which can be burned directly. It has the further benefit of economy while diminishing the possibility of perpetuating a contaminated culture.

When desired, the aqueous phase can be withdrawn from the separation zone and passed such as by line 34 to a separate sulfate removal zone 40. In this or other zone (not shown) the aqueous phase may be first treated, such as by flocculation and/or filtration, to remove any cellular or other suspended material. The cellular material may be reused in cellular form or as an extract.

The desulfurized bitumen can then be withdrawn such as by line 32 and stored, burned, reemulsified or refined. Desirably, in the case of very heavy bitumens such as Orinoco bitumens and others, it can be reemulsified as a desulfurized oil-in-water emulsion to assist in its storage and handling. Alternatively, it can be prepared as an oil-in-water emulsion fuel for combustion or further treatment. Combustion of heavy oil-in-water emulsions is well known to those skilled in the art, and may require modifications to burner nozzles to optimize combustion. It is an advantage of the invention that when Orimulsion fuel emulsions are treated by the process of this invention, they can very easily be employed to replace coal with reduced $SO_x$ and particulates.

The aqueous phase in zone 40 contains microorganisms, water and sulfur. Following separation of cellular or suspended material, the sulfur can be removed from the remaining liquid by the addition of a calcium, magnesium, aluminum or barium based water treatment/precipitating agent, and separation of solids. Separation of the precipitated sulfates can be made at line 42 and the water and microorganisms can be recycled back to the desulfurization step via conduit 44. If excess or unwanted organisms have evolved, then they can be directed as a waste stream for combustion or disposal. It is possible that new or regenerated organisms may need to be added to the recycle stream to replace those eliminated or killed in the overall process.

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

This example describes the desulfurization of Orimulsion bitumen-in-water emulsion.

An open barrel containing 30 gallons of emulsion is employed as the reactor. The barrel is held in a vat of water which is controlled to maintain the temperature at about 30° C. A sparging ring is positioned at the bottom of the barrel to deliver air into the emulsion at a rate of 100 liters per minute. The emulsion has the following analysis:

|  | Parts (wt.) |
|---|---|
| Moisture | 28.56 |
| Carbon | 60.85 |
| Hydrogen | 7.12 |
| Sulfur | 2.69 |
| Nitrogen | 0.48 |
| Oxygen | 0.09 |
| Ash | 0.21 |
|  | 100.00 |
| Metals | (ppm) |
| V | 324 |
| Ni | 74 |
| Fe | 14 |
| Na | 78 |
| Mg | 473 |
| Spec. Gravity (°API) | 8.6 |
| Flash Point, °C. | 102 |
| Distillation % vol IBP-343, °C. | 10.9 |
| Droplet Size Distribution Mean size, microns | 15.5 |
| Apparent Viscosity | (cP at 30° C.) |
| @ 10 sec$^{-1}$ | 932 |
| @ 50 sec$^{-1}$ | 690 |
| @ 100 sec$^{-1}$ | 582 |
| Kinematic Viscosity |  |
| 50° C. | $\geq$10,000 centistokes |
| 80° C. | $\geq$1,000 centistokes |

Separately, a culture is prepared as in U.S. Pat. No. 4,632,906. The organism (ATCC No. 39909) is a strain of *Bacillus sulfasportare* which has the ability to oxidize organic sulfur to water-soluble sulfates and utilize carbon dioxide as its sole source of carbon.

The aqueous phase of the emulsion is supplemented with minerals to sustain the growth of the culture and 1 liter of culture (containing $10^9$ cells per milliliter) is added to the reactor. Reaction is continued for 30 days with continued air sparging gently to agitate and supply of oxygen and carbon dioxide to sustain the reaction. The aqueous phase is analyzed daily for pH and sulfate. The reaction mixture is manually agitated twice daily with a large paddle to minimize the problems with channeling and poor distribution of oxygen to the culture. Magnesium carbonate is added as necessary to maintain the pH between 6 and 8. The fuel is burned in this form without removal of the cells or sulfate salts, simply straining prior to atomization by steam or air to assure that the injection nozzles are not clogged. The sulfates are bound by the magnesium and not available for the formation of $SO_x$.

EXAMPLE 2

The process of Example 1 is repeated, but this time the sulfur content of the emulsion is determined prior to reaction, and a stoichiometric amount of finely-divided dolomite is admixed with the emulsion at the beginning of the reaction. Periodic additions of magnesium carbonate are not employed.

EXAMPLE 3

The process of Example 1 is again varied, this time the emulsion is transferred to a large vat after reaction and is there flooded with 300 gallons of water at 30 degrees Celsius. This treatment at least partially breaks the emulsion, permitting an aqueous layer to be decanted and the mass of live cells to be recovered. The resulting bitumen layer is then reheated and reemulsified.

EXAMPLE 4

The process of Example 3 is repeated, but this time after separating the aqueous layer and recovering the live cells, calcium hydroxide is added in 10% excess of the sulfate to precipitate the sulfate as calcium sulfate which can be recovered and employed in the manufacture of gypsum products.

EXAMPLE 5

The process of Example 3 is again repeated, but this time the recovered cells are macerated to prepare an extract.

EXAMPLE 6

Ten gallons of Orimulsion fuel emulsion are placed in a reactor as in Example 1, to this are added: (1) an additional fifteen gallons of water, (2) calcium carbonate, in stoichiometric amount with the sulfur in the fuel, and (3) a cell extract as prepared in example 5. The reaction is then carried out as in Example 1.

EXAMPLE 7

Ten gallons of Orimulsion fuel emulsion are placed in a reactor as in example 1, to this are added an inoculum of *Rhodococcus rhodochrous* IGTS8, and the reaction is then carried out as in Example 1.

EXAMPLE 8

The process of Example 7 is repeated but this time the emulsion is transferred to a pressure vessel following reaction and heated to about 110° C. to break the emulsion. The phases are separated and the bitumen is reemulsified with sufficient water to provide an emulsion with 30% water.

EXAMPLE 9

The procedure for Example 7 is repeated, but this time employing a culture of *Bacillus sphaericus* IGTS9, an additional five gallons of water is added before the reaction, no magnesium carbonate is added during reaction, and following reaction calcium hydroxide is added to the reaction mixture in stoichiometric quantity with the original sulfur content of the fuel.

EXAMPLE 10

The process of Example 7 is repeated, but this time the organism is *B. sphaericus* IGTS9, the emulsion is broken chemically following reaction, and the aqueous phase is separated and treated with alumina trihydrate.

EXAMPLE 11

The process of Example 10 is repeated, but this time an additional ten gallons of water are added prior to the reaction, and the reaction is carried out in three stages, each of ten days duration. After each stage, the emulsion is broken by heat and pressure and the bitumen reemulsified with a fresh aqueous phase. Following the third stage reaction, the water for emulsification is reduced to three gallons.

EXAMPLE 12

The process of Example 11 is repeated, but this time the emulsion is preliminarily broken by causing pressure drop through a ball valve with exit to an open vat wherein at least a portion of the live cells are recovered for use in subsequent processing.

EXAMPLE 13

The process of Example 1 is repeated, but this time employing a mixed culture of *B. sphaericus* IGTS9 and *B. Sulfasportare* ATCC 39909 and following reaction, adding a stoichiometric amount of alumina trihydrate based on the original sulfur content of the fuel.

EXAMPLE 14

The process of Example 13 is repeated wherein the emulsion is then broken after reaction, the cells are separated from the aqueous phase prior to addition of the alumina trihydrate and the bitumen is reemulsified to achieve an emulsion containing 30% water.

EXAMPLE 15

The process of Example 1 is repeated with several variations. In this Example, the emulsion is contacted with *Rhodococcus rhodochrous* IGTS8, again for thirty days and again at 30° C. Following reaction, the reaction mixture is transferred to a large vat and is there flooded with 300 gallons of water at 30 degrees Celsius. This treatment at least partially breaks the emulsion, permitting an aqueous layer to be decanted and the mass of live cells to be recovered. The water phase is then reacted with a twenty percent excess of calcium oxide to precipitate the sulfates. The resulting bitumen layer is then reheated and reemulsified.

EXAMPLE 16

Four 125 ml flasks were prepared as follows

Flasks contained 50 ml of an aqueous solution of inorganic mineral salts, 5 µl of a commercial surfactant (Zonyl FSN™), 400 mg of a commercial emulsion of bitumen in water (Orimulsion) and 20 mM glycerol as a carbon source. Two of the above flasks were then inoculated with *Rhodococcus rhodochrous* IGTS8 (ATCC No. 53968) culture grown for eight days at an inoculum strength of $4.5 \times 10^{10}$ cells per flask; while the other two flasks were not inoculated and used as controls.

Incubation of all flasks was for 19 days at 29° C. with shaking at 175 rpm. Porous stoppers were used in the flasks to allow for oxygen transfer.

Following incubation the samples were centrifuged to recover the bitumen from the water and cells, and the bitumen was analyzed for sulfur, carbon, nitrogen, hydrogen and oxygen. The following data summarize the means of duplicate analyses for each test criteria:

| Treatment | % C | % H | % O | % N | % S | TOTAL | C/S |
|---|---|---|---|---|---|---|---|
| R. rhodochrous | 72.9 | 9.7 | 6.6 | 0.66 | 3.0 | 93.0 | 24.3 |
|  | 71.7 | 9.5 | 10.0 | 0.82 | 2.5 | 94.5 | 28.8 |
| no cells | 77.2 | 10.0 | 7.8 | 0.68 | 3.3 | 99.0 | 23.8 |
|  | 76.5 | 10.0 | 6.9 | 0.68 | 3.5 | 97.6 | 21.6 |

EXAMPLE 17

A test was run similar to that in Example 16, but using 600 mg of Orimulsion and a higher cell density of $1.4 \times 10^{11}$ cells per flask. Growth was for seven days with incubation for 10 days. The results are shown below:

| Treatment | % C | % H | % O | % N | % S | TOTAL | C/S |
|---|---|---|---|---|---|---|---|
| R. rhodochrous | 77.15 | 9.86 | 7.45 | 1.07 | 3.20 | 99.23 | 24.11 |
|  | 77.97 | 10.03 | 6.24 | 1.69 | 3.15 | 99.08 | 24.75 |
| no cells | 83.30 | 10.21 | 1.18 | 0.74 | 3.83 | 99.26 | 21.75 |
|  | 83.35 | 10.24 | 1.08 | 0.77 | 3.82 | 99.26 | 21.82 |

The above description is for the purpose of teaching the person of ordinary skill in the art how to practice the invention, and it is not intended to detail all those obvious modifications and variations of it which will become apparent to the skilled worker upon reading the description. For example, the advantages of this invention have application to other hydrocarbons, including coal and other crudes and petroleum fractions. It is intended that all such reasonable modifications and variations be included within the scope of the invention, which is defined by the following claims.

I claim:

1. A process for desulfurizing bitumen containing sulfur and exhibiting a kinematic viscosity of at least about 10,000 centistokes at 50° C., to reduce the oxidizable sulfur content of the bitumen in a bitumen-in-water emulsion, comprising:

contacting the bitumen-in-water emulsion with a microbiological desulfurization agent;

maintaining contact at a temperature of less than about 50° C. under conditions effective to convert at least a portion of the sulfur content of the bitumen to sulfate oxidation products;

at least partially breaking the emulsion following reaction to produce a separable aqueous layer containing the majority of the desulfurization agent and sulfate oxidation products;

separating the aqueous layer containing the sulfate oxidation products from the bitumen;

and recovering the desulfurized bitumen so produced.

2. A process according to claim 1 wherein the emulsion is agitated in an open reactor vessel.

3. A process according to claim 1 which further includes:
adding to the aqueous phase a $SO_x$-binding agent selected from the group consisting of the oxides, hydroxides, or carbonates of calcium, magnesium, aluminum, and barium.

4. A process according to claim 3 wherein, following separation, the aqueous layer is treated to remove the desulfurization agent, and the resulting aqueous liquid is then treated by the addition of the $SO_x$-binding agent.

5. A process according to claim 1 further comprising the steps of reemulsifying the bitumen in from 2 to 10 stages of emulsification, contact, breaking the emulsion, separation of the aqueous layer from the bitumen and reemulsifying the bitumen to recover further purified bitumen.

6. A process according to claim 5 wherein the emulsion is agitated in an open reactor vessel during contact with a culture of live cells as the desulfurizing agent.

7. A process according to claim 5 wherein the desulfurization agent is recovered and employed in at least one additional stage.

8. A process according to claim 1 wherein the emulsion is broken by heating.

9. A process according to claim 1 wherein the emulsion is broken by adding a deemulsifying chemical agent.

10. A process according to claim 1 wherein the emulsion is broken by subjecting the emulsion to shear.

11. A process according to claim 1 wherein the emulsion is broken by introducing water, after which a portion of the aqueous phase is separated to recover the desulfurization agent.

12. A process according to claim 7 wherein the desulfurization agent comprises live cells which are recovered and processed to make a cell extract.

13. A process for reducing production of $SO_x$ resulting from burning bitumen containing sulfur and exhibiting a kinematic viscosity of at least about 10,000 centistokes at 50° C. in a bitumen-in-water emulsion, comprising:

contacting the bitumen-in-water emulsion with a microbiological desulfurization agent selected from the group consisting of cell cultures, immobilized cell masses, fragmented cells, cell extracts, enzyme mixtures, synthetically-prepared copies of active enzyme sequences or components, and mixtures of these;

maintaining contact at a temperature of less than about 50° C. under conditions effective to reduce the oxidizable sulfur content of the bitumen;

adding $SO_x$-binding chemical to the water in the aqueous phase of the emulsion; and burning the emulsion.

14. A process according to claim 13 wherein the emulsion is broken after contact of the bitumen with the microbiological desulfurization agent, the bitumen is separated from a majority of the desulfurization agent, and the bitumen is reemulsified and contacted at least one more time with desulfurization agent.

15. A process according to claim 13 wherein the emulsion is broken after contact of the bitumen with the microbiological desulfurization agent, the desulfurization agent is separated from the bitumen, and the bitumen is reemulsified with water prior to burning.

16. A process for desulfurizing bitumen in a stable bitumen-in-water emulsion containing about 30% to 70% water, said bitumen containing sulfur and exhibiting a kinematic viscosity of at least about 10,000 centistokes at 50° C. and a droplet size in the emulsion of between about 10µ and about 100µ, comprising:

contacting the bitumen-in-water emulsion with a microbiological desulfurization agent in a large open stirred reactor;

maintaining contact at a temperature of less than about 50° C. for a time and under conditions effective to reduce the oxidizable sulfur content of the bitumen.

17. A process according to claim 16 wherein the desulfurization agent comprises a member selected from the group consisting of cell cultures, immobilized cell masses, fragmented cells, cell extracts, enzyme mixtures, synthetically-prepared copies of active enzyme sequences or components, and mixtures of these derived from *Rhodococcus rhodochrous* ATCC 53968.

18. A process according to claim 16 wherein the pH is controlled by the addition of a calcium or magnesium compound.

19. A process according to claim 16 wherein a $SO_x$-binding chemical is added to the bitumen-in-water emulsion in contact with the microbiological desulfurization agent.

20. A process according to claim 16 wherein the emulsion is at least partially broken following contact with the microbiological desulfurization agent.

* * * * *